United States Patent
Angot et al.

(10) Patent No.: US 9,744,693 B2
(45) Date of Patent: Aug. 29, 2017

(54) METHOD FOR MANUFACTURING A CONNECTOR

(71) Applicants: Maxime Angot, Ahetze (FR); Francois Capitaine, Anglet (FR)

(72) Inventors: Maxime Angot, Ahetze (FR); Francois Capitaine, Anglet (FR)

(73) Assignee: TECHNOFLEX, Bidart (FR)

( * ) Notice: Subject to any disclaimer, the term of this patent is extended or adjusted under 35 U.S.C. 154(b) by 453 days.

(21) Appl. No.: 14/312,966

(22) Filed: Jun. 24, 2014

(65) Prior Publication Data
US 2014/0374961 A1   Dec. 25, 2014

(30) Foreign Application Priority Data
Jun. 25, 2013 (FR) .................................. 13 56082

(51) Int. Cl.
| | | |
|---|---|---|
| *B29C 33/08* | (2006.01) | |
| *A61M 39/10* | (2006.01) | |
| *B29D 23/00* | (2006.01) | |
| *B29C 67/00* | (2017.01) | |

(52) U.S. Cl.
CPC ............. *B29C 33/08* (2013.01); *A61M 39/10* (2013.01); *B29C 67/0022* (2013.01); *B29C 67/0048* (2013.01); *B29D 23/003* (2013.01)

(58) Field of Classification Search
CPC ... H01R 13/5224; A61M 30/10; A61M 39/10; B29C 33/08; B29C 67/0022; B29C 67/0048; B29C 31/002; B29C 33/485; B29C 33/505; B29C 53/42; B29C 53/50; B29C 53/60; B29C 57/00; B29D 23/003
See application file for complete search history.

(56) References Cited

U.S. PATENT DOCUMENTS 5,681,296 A * 10/1997 Ishida ............... A61M 25/0009
600/585

* cited by examiner

*Primary Examiner* — Stella Yi
(74) *Attorney, Agent, or Firm* — Young & Thompson

(57) ABSTRACT

A method and apparatus for manufacturing a connector for a container for medical use intended to administer fluid, the connector including a main body defining an inner channel for fluid to pass through and at least one continuous or discontinuous bead, projecting inside the channel. The method includes:
a) producing a tubular conduit with no bead projecting inside the channel,
b) inserting at least partially into the tubular conduit a mandrel having, on its outer surface, at least one continuous or discontinuous annular recess, whose dimensions and shape correspond to those of a continuous or discontinuous bead to be formed in the inner channel,
c) partially heating the tubular conduit, the part including at least the conduit portion placed at the at least one recess when the mandrel has been positioned in the tubular conduit, such that the material of the tubular conduit fills the at least one recess.

7 Claims, 4 Drawing Sheets

METHOD FOR MANUFACTURING A CONNECTOR

BACKGROUND OF THE INVENTION

Field of the Invention

The present invention relates to flexible containers for medical use and particularly relates to a method for manufacturing a connector for such flexible bags.

It also relates to an apparatus for implementing this method for manufacturing a connector.

Technical Background

Elements for accessing the content of a flexible bag intended to contain a liquid for medical use in order to fill and empty this bag are known.

Such an access element generally takes the form of a shaft, which is formed by a tube portion being inserted between the two constituent inert plastic walls of the flexible bag and assembling the resulting assembly by binding together at least the peripheral edges of these walls.

One end of this tube portion is in fluid communication with the interior volume of the flexible bag while the other end thereof is placed outside the bag.

To establish liquid communication between the inside of the flexible bag and the outside, an operator then only has to manually insert the end of a connecting piece into this shaft.

To seal the link between the end of this connecting piece and the shaft, it is generally envisaged to position a ring on the inside wall of the shaft defining the liquid passage channel.

This ring which then projects from the inside wall of the shaft into said channel provides an angular linear contact between this wall and the connecting piece.

In addition to sealing the assembly, this contact also limits the effort required for tightening during the assembly of these elements.

The manufacture of such a ring in the inner channel of the shaft is, however, made difficult by the very nature of the materials used in the medical field.

Indeed, these connecting pieces are generally obtained by injecting a thermoplastic material into a mould, spindles being used to define the inner channel for flow of the liquids in these connecting pieces and to define the ring.

Therefore, if the positioning of such a ring in the channel of a shaft formed from a relatively rigid thermoplastic material such as polypropylene (PP) is achievable, it becomes laborious for flexible and/or adhesive thermoplastic materials such as ethylene vinyl acetate (EVA) or EVA derivatives, in particular those compliant with the pharmacopoeia requirements.

Indeed, during the removal of the spindles, there is an extraction of material or the appearance of permanent deformations which require the withdrawal of the shaft formed in this manner.

However, these thermoplastic materials such as EVA tend to stand out compared to the other materials for the manufacture of the elements for storing and conveying liquid for medical use as a result of the inertia thereof in relation to medical solutions, the resistance thereof to radiation sterilisation and the performance thereof at low temperature.

Moreover, producing such connectors from EVA would be particularly advantageous since the availability thereof would allow the manufacture of a flexible bag for medical use produced fully from the same thermoplastic material, and consequently, would make the assembly thereof easier.

The present invention aims to overcome these various disadvantages by proposing a method for manufacturing a connector for a flexible bag for medical use which is particularly simple in the design thereof and in the operating process thereof, which is original in the approach thereof and economical, for producing a ring on the inside wall of the connector without any damage thereof.

Another subject matter of the invention is an apparatus which is original in terms of the architecture thereof for industrially producing these connectors with limited production times.

BRIEF DESCRIPTION OF THE INVENTION

To this end, the invention relates to a method for manufacturing a connector for a container for medical use intended for the administration of fluid, said connector comprising a main body defining an inner channel for a fluid to pass through and at least one continuous or discontinuous bead, projecting inside said channel.

According to the invention, at least the following steps are carried out:

a) a tubular conduit with no bead projecting inside said channel is taken as a starting point, b) inserted at least partially into said tubular conduit formed in this manner is a mandrel having, on the outer surface thereof, at least one continuous or discontinuous annular recess, the dimensions and the shape of which correspond to those of a continuous or discontinuous bead to be formed in the inner channel of said conduit, c) said tubular conduit is only partially heated, said part comprising at least said conduit portion placed at said at least one recess when said mandrel has been positioned in said tubular conduit, such that the material of said tubular conduit fills said at least one recess.

Of course, the straight cross-section of this recess cannot be round or substantially round but can, by contrast, have one or more flat, rounded, bulged, elliptical, etc, walls, and combinations of these elements.

More generally, the mandrel includes, on the outer surface thereof, a continuous or discontinuous recess which is the mould, or the negative, for the object to be formed in a projecting manner on the inside wall of the connector defining the fluid passage channel. Therefore, to define a bead, or ring, on this wall, the outer surface of the mandrel includes a recess completely surrounding or describing the circumference of this mandrel.

The connector obtained according to the method of the invention is particularly suitable for establishing fluid communication, of the liquid or liquid/powder mixture type, in a fluid conveying circuit for medical use.

Moreover, since the or each ring is obtained by the plastic deformation of the molten material of the locally heated tubular conduit, the final connector is made from one piece.

The "connector being made from one piece" means that this connector is all in one piece and is not the result of assembling initially separate pieces.

By way of illustration only, this connector can be produced from a medically inert thermoplastic material such as EVA, derivatives of EVA, made from polyethylene, acrylate derivatives such as ethylene-methyl acrylate (EMA), made from polyolefin comprising a thermoplastic elastomer (TPE) such as SEB (styrene-ethylene-butylene block copolymer), SEBS (styrene-ethylene-butylene-styrene block copolymer), etc.

Furthermore, the method of the invention is particularly quick to implement and, therefore, allows industrial production of these connectors with low manufacturing costs.

In various specific embodiments of this method, each having specific advantages thereof which can have numerous possible technical combinations:

said mandrel is cooled before removing the latter from the inner channel of said tubular conduit, in step c), heating takes place using a heating method chosen from:

dielectric heating, such as high-frequency heating, radiation such as with laser beams, or direct contact with heated elements.

Advantageously, when implementing a dielectric heating method, said mandrel is used as one of said electrodes.

in step a), a tubular conduit is formed which comprises at least one element for obstructing said channel, said at least one obstruction element being breakable in order to clear the passage.

Advantageously, a sealing membrane is formed inside said channel for ensuring the asepsis of the content of the container with which the connector will be assembled.

Preferably, this sealing membrane will be positioned in the inner channel in order to form an abutment for stopping the movement of the mandrel when it is inserted into this channel in order to position said or each bead at one or more precise points of this channel.

This sealing membrane is intended to be subsequently separated by means of a trocar puncture needle in order to clear the access to the inner channel. This sealing membrane is, preferably, made breakable by a line of least resistance. Furthermore, it can include a reinforcement area on the circumference thereof in order to prevent a possible insertion into the liquid circuit to which the connector of the invention would be connected of a piece thereof following tearing.

This sealing membrane also ensures ideal positioning of the annular recess in relation to the second electrode, and consequently the precise bead positioning inside the inner channel. Such a precise positioning of the bead is important for ensuring the impermeability of the trocar puncture needle/connector assembly.

More generally, an obstruction element is formed at the end of said tubular conduit and/or inside said channel, this then being a sealing membrane.

The obstruction element placed at the end of said conduit can be a cap, a twist-off cap, a lid or a combination of these elements.

in step a), a chamfer is produced at at least one of the ends of said body conduit such that at least one of said ends is beveled and/or on the outer surface of said body conduit is formed one or more elements chosen from the group comprising a ring, a threading, a helical groove, a collar and a joining element which can be incorporated in the flexible container, this joining element including, at each of the side edges thereof, a blade, these blades each forming an extension of the central part of this joining element, etc.

The invention also relates to an apparatus for implementing the manufacturing method as described above.

According to the invention, this apparatus comprises:

a high-frequency electric generator suitable for providing a high-frequency voltage, a first tubular electrode having a diameter equal or substantially equal to the diameter of the inner channel of said tubular conduit such as to be able to be inserted into said inner channel, said first electrode including, on the outer surface thereof, at least one continuous or discontinuous annular recess, the dimensions and the shape of which correspond to those of a continuous or discontinuous bead to be formed in the inner channel of said conduit, a second electrode including a hole having a diameter less than or equal to the outer diameter of said tubular conduit such as to define a housing for receiving and surrounding, in part, said conduit.

The apparatus can further comprise a means for cooling said first electrode such as a water cooling system.

Advantageously, since the inner channel of said conduit includes a breakable sealing membrane, the free end of said first tubular electrode has a blunt contact surface for placing it flush against said sealing membrane without tearing it.

This sealing membrane then has the function of a marker or reference point for precisely placing the bead in the inner channel such as to seal the trocar puncture needle/tubular conduit assembly.

Since the inner channel of said conduit includes a breakable sealing membrane, the longitudinal dimension separating the or each recess of said first electrode and the free end thereof is at least equal to the distance that is to separate said sealing membrane and the or each bead in order to seal the assembly of said conduit and of the corresponding trocar puncture needle.

BRIEF DESCRIPTION OF THE DRAWINGS

Other advantages, aims and specific features of the present invention will emerge from the following description, which is given for explanation purposes and is in no way limiting, with reference to the appended drawings, wherein.

DETAILED DESCRIPTION OF EMBODIMENTS OF THE INVENTION

It will firstly be noted that the figures are not to scale.

Figure 1:
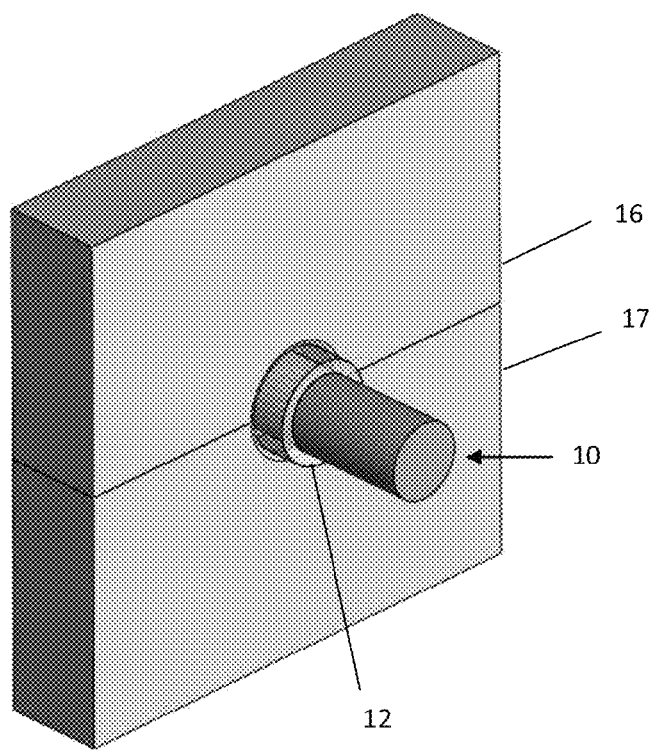
FIG. 1 is a partial and perspective view of an apparatus for manufacturing a connector according to a particular embodiment of the present invention, a connector being positioned in this apparatus in order to form a ring in the inner channel thereof.
Figure 2:
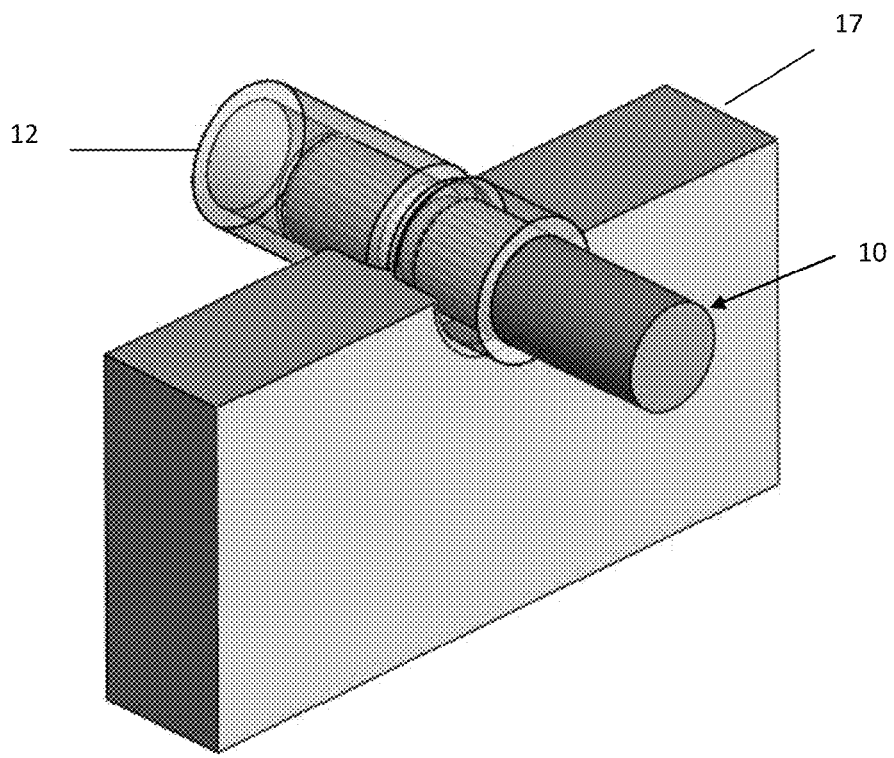
FIG. 2 is a partial and perspective view of the apparatus of FIG. 1; the upper half-electrode has been omitted for the purpose of clarity.
Figure 3:
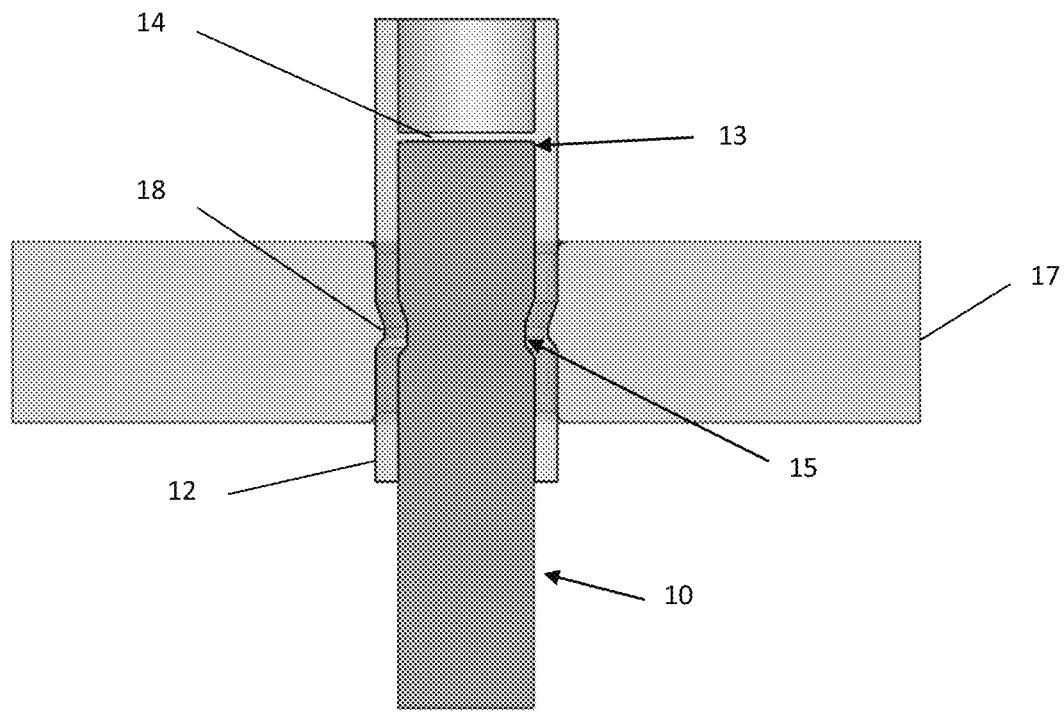
FIG. 3 is an enlarged sectional view of the apparatus of FIG. 1.
Figure 4:
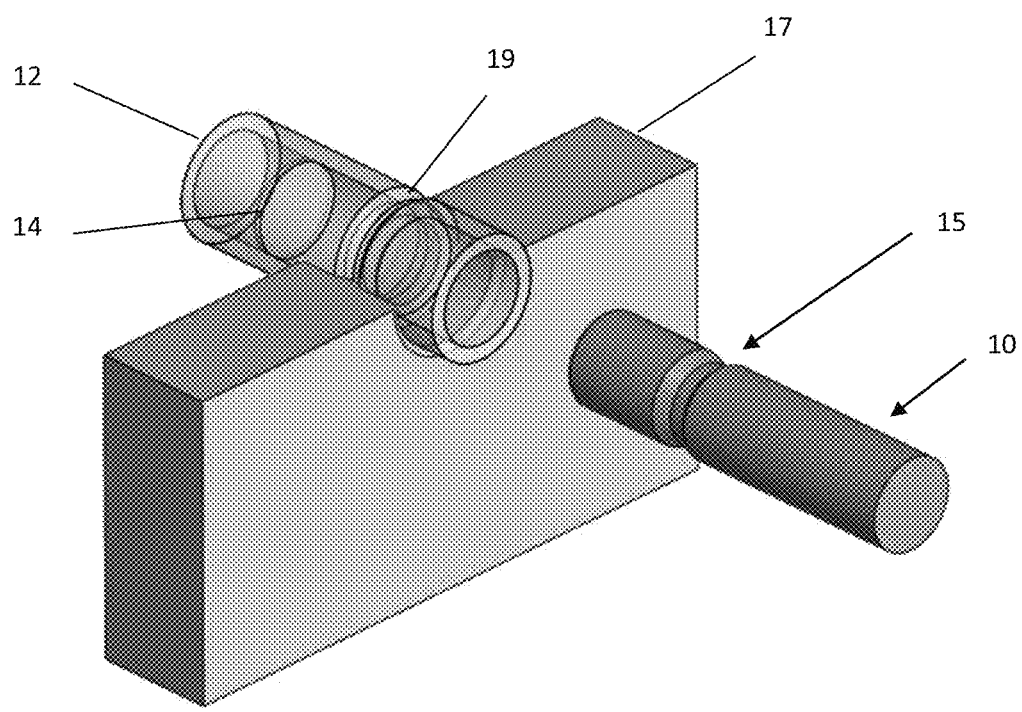
FIG. 4 is a partial and perspective view of the apparatus of FIG. 1; the upper half-electrode has been omitted for the purpose of clarity and the mandrel has been removed from the body of the connector following formation of the ring.
Figure 5:
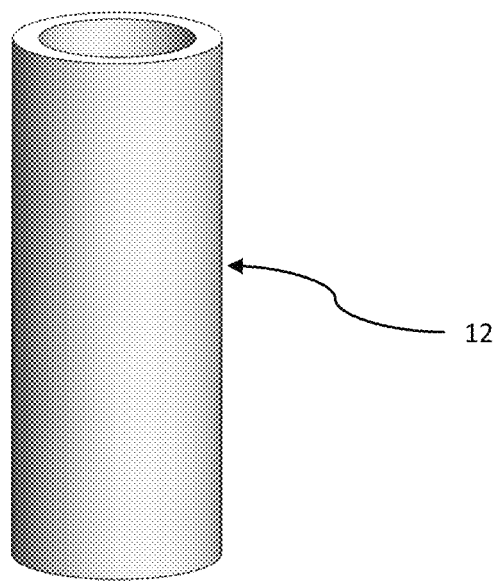
FIG. 5 is a perspective view of a tubular conduit in which a ring is to be formed according to an embodiment of the present invention.
Figure 6:
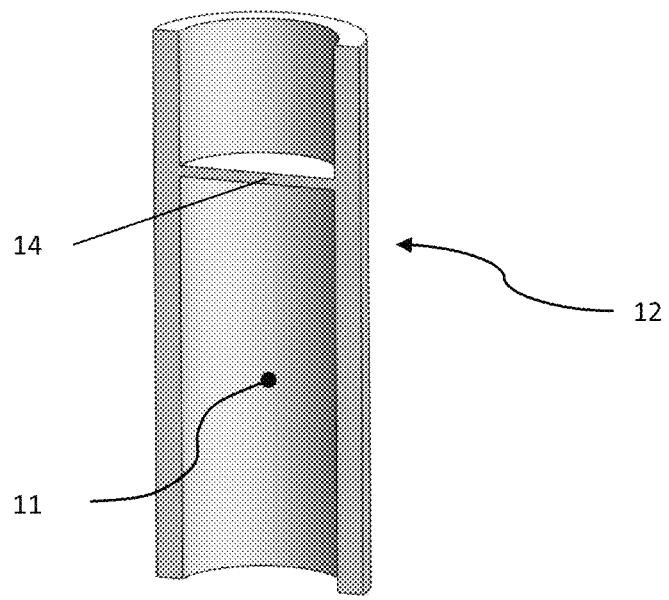
FIG. 6 is a longitudinal sectional view of the tubular conduit of FIG. 5 showing the fluid passage inner channel which does not have a ring but is blocked by a membrane.
Figure 7:
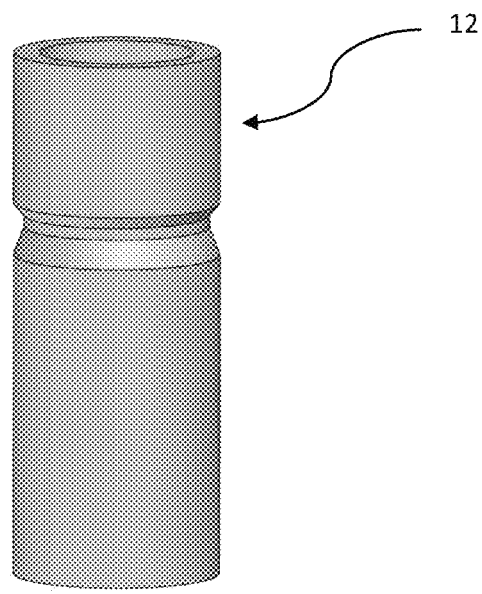
FIG. 7 is a perspective view of a connector according to a specific embodiment of the present invention.
Figure 8:
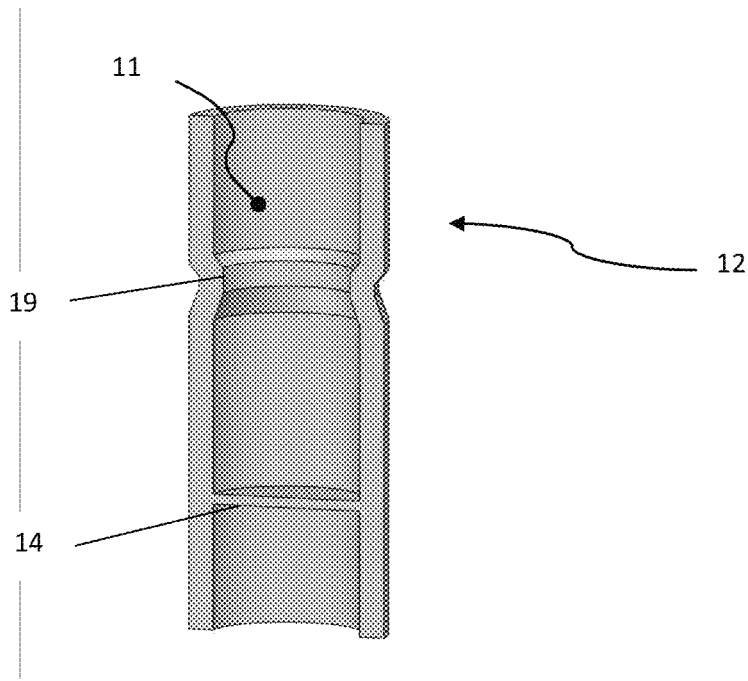
FIG. 8 is a longitudinal sectional view of the connector of FIG. 7 showing the fluid passage inner channel blocked by a membrane and including a ring.

To produce a connector including a ring placed on the inside wall thereof defining a channel for a fluid to pass through, the operator obtains or manufactures, firstly, a tubular conduit 12 which does not have a ring projecting into the inner channel 11 thereof (FIGS. 5 and 6). This tubular conduit 12 advantageously includes a sealing membrane 14, the function of which will be described below.

This tubular conduit 12 can, for example, be produced using a known method of injecting a plastic, such as EVA, into a mould.

Once this tubular conduit 12 has been selected or manufactured, the operator can then produce one or more rings inside the channel thereof.

FIGS. 1-4 show an apparatus for manufacturing a connector according to a preferred embodiment of the invention.

This apparatus comprises a high-frequency electric generator (not shown) which can provide a high-frequency voltage. In this case, this generator can provide signals at frequencies greater than a few dozen MHz.

This electric generator is connected by a power transmission line (not shown) to a first tubular electrode 10, the diameter of which is substantially equal to the diameter of the inner channel 11 of the tubular conduit 12 such as to be inserted into this channel. This power transmission line is, in this case, a coaxial cable.

The free end 13 of this first electrode 10 which is intended to be inserted into the inner channel 11 of the tubular conduit 12 has a flat or substantially flat face allowing the operator to feel this free end 13 contacting the sealing membrane 14 blocking the inner channel 11 of the tubular conduit 12 without a risk of damaging this membrane.

In this case, this sealing membrane 14 has the function of a marker or reference point, for precisely positioning the first electrode 10 inside the inner channel 11.

Therefore, it is ensured that the annular recess 15 placed on the outer surface of the first electrode 10 is positioned precisely at a distance d from this sealing membrane 14. Observing this distance d is, indeed, necessary for ensuring the impermeability of the trocar puncture needle/connector link.

Advantageously, this annular recess 15 has a shape and dimensions which make it the mould, or the negative, for the ring to be produced on the inside wall of the tubular conduit 12, this ring being placed in a projecting manner in the inner channel of the connector. This recess 15 which describes the circumference of the outer surface of the mandrel 10 has a straight cross-section comprising a combination of a flat central wall which is parallel or substantially parallel to the longitudinal axis of the mandrel 10 and two inclined flat end walls placed at the ends of the central wall. The inclined flat wall which is closest to the sealing membrane 14 has a slope which helps the mandrel 10 to be removed from the tubular conduit 12 following the formation of the ring.

The assembly assembled in this manner is placed in a second electrode comprising a hole in the central part thereof which has a diameter that is less than the outer diameter of the tubular conduit 12 such as to receive and pinch this tubular conduit 12 in order to form the ring.

This second electrode comprises two half-electrodes 16, 17, one electrode 16 of these half-electrodes being movable in relation to the other half-electrode 17 such as to able to be moved apart from and brought closer to the latter in order to provide optimum positioning of the tubular conduit 12/first electrode 10 assembly.

Indeed, the aim will be to only locally heat the tubular conduit 12 in order to form the ring on the inside wall of the tubular conduit 12 by transfer of molten material of a portion solely of this tubular conduit 12 into the annular recess 15.

This transfer of material creates a local deformation of the outer surface of the tubular conduit 12 which is in no way restrictive for the latter to operate correctly.

To facilitate heating and the transfer of molten material towards the annular recess 15 of the mandrel 10, each half-electrode 16, 17 has, on the surface defining part of the contour of the hole for receiving the tubular conduit 12/first electrode 10 assembly, a bulged surface projecting to press this assembly at the recess 15 of the mandrel 10 when the latter is in position in the second electrode. This bulged surface which follows the contour of the hole forms, in this case, a tooth 18 for each half-electrode 16, 17. Advantageously, this bulged surface has a shape complementary to that of the recess 15 of the mandrel 10.

The apparatus further includes a means for cooling (not shown) the first electrode 10 such as a cooled water cooling device.

In an embodiment of the present invention, and for a tubular conduit made from EVA, providing heat via the two half-electrodes 16, 17, i.e. approximately 80° C. for approximately three (3) seconds, allows the ring 19 to be produced by the plastic deformation of the molten material of the portion of the tubular conduit 12 which has been heated in this manner.

If the first electrode 10, which is, for example, made from brass, is not temperature-controlled, it is necessary to wait for the connector to have cooled substantially before removal. The resulting ring 19 is then no longer at risk of being damaged by the friction of the recess 15 of the first electrode 10.

The invention claimed is:

1. A method for manufacturing a connector for a container for medical use intended for administration of fluid, said connector comprising a main body defining an inner channel (11) for a fluid to pass through and at least one continuous or discontinuous bead (19), projecting inside said channel, wherein at least the following steps are carried out:
   a) a tubular conduit (12) with no bead (19) projecting inside said channel is taken as a starting point,
   b) inserted at least partially into said tubular conduit (12) formed in this manner is a mandrel having, on the outer surface thereof, at least one continuous or discontinuous annular recess (15), the dimensions and the shape of which correspond to those of a continuous or discontinuous bead (19) to be formed in the inner channel (11) of said conduit,
   c) said tubular conduit (12) is only partially heated, said connector comprising at least said tubular conduit placed at said at least one continuous or discontinuous annular recess (15) when said mandrel has been positioned in said tubular conduit (12), such that a material of said tubular conduit (12) fills said at least one continuous or discontinuous annular recess (15), wherein in step c), heating takes place using a heating method chosen from dielectric heating, radiation and direct contact with heated elements, and when implementing a dielectric heating method, said mandrel is used as one of said electrodes.

2. The method according to claim 1, wherein said mandrel is cooled before removing the mandrel from the inner channel (11) of said tubular conduit (12).

3. A method for manufacturing a connector for a container for medical use intended for administration of fluid, said connector comprising a main body defining an inner channel (11) for a fluid to pass through and at least one continuous or discontinuous bead (19), projecting inside said channel, wherein at least the following steps are carried out:
   a) a tubular conduit (12) with no bead (19) projecting inside said channel is taken as a starting point,
   b) inserted at least partially into said tubular conduit (12) formed in this manner is a mandrel having, on the outer surface thereof, at least one continuous or discontinuous annular recess (15), the dimensions and the shape of which correspond to those of a continuous or discontinuous bead (19) to be formed in the inner channel (11) of said conduit, c) said tubular conduit (12) is only partially heated, said connector comprising at least said tubular conduit placed at said at least one continuous or discontinuous annular recess (15) when said mandrel has been positioned in said tubular conduit (12), such that a material of said tubular conduit (12) fills said at least one continuous or discontinuous annular recess (15), wherein, in step a), a tubular conduit (12) is formed which comprises at least one element for obstructing said channel, said at least one obstruction element being breakable in order to clear the channel.

4. The method according claim 3, characterized in that wherein a sealing membrane is formed inside said channel, said sealing membrane being positioned in said channel in order to form an abutment for stopping the movement of the mandrel when it is inserted into said channel in order to position said continuous or discontinuous bead (19) at one or more precise points of said channel.

5. A method for manufacturing a connector for a container for medical use intended for administration of fluid, said connector comprising a main body defining an inner channel (11) for a fluid to pass through and at least one continuous or discontinuous bead (19), projecting inside said channel, wherein at least the following steps are carried out:

a) a tubular conduit (12) with no bead (19) projecting inside said channel is taken as a starting point, b) inserted at least partially into said tubular conduit (12) formed in this manner is a mandrel having, on the outer surface thereof, at least one continuous or discontinuous annular recess (15), the dimensions and the shape of which correspond to those of a continuous or discontinuous bead (19) to be formed in the inner channel (11) of said conduit, c) said tubular conduit (12) is only partially heated, said connector comprising at least said tubular conduit placed at said at least one continuous or discontinuous annular recess (15) when said mandrel has been positioned in said tubular conduit (12), such that a material of said tubular conduit (12) fills said at least one continuous or discontinuous annular recess (15), wherein in step a), a chamfer is produced at at least one of the ends of said tubular conduit such that at least one of said ends is beveled and/or on the outer surface of said tubular conduit is formed at least one of the elements chosen from the group comprising one or more projecting rings, a joining element which can be incorporated in the container, this joining element including, at each of the side edges thereof, a blade, these blades each forming an extension of the central part of this joining element.

6. The method according to claim 3, wherein, in step c), heating takes place using a heating method chosen from dielectric heating, radiation and direct contact with heated elements.

7. The method according to claim 5, wherein, in step c), heating takes place using a heating method chosen from dielectric heating, radiation and direct contact with heated elements.

* * * * *